United States Patent
Zacche' et al.

(10) Patent No.: US 8,853,395 B2
(45) Date of Patent: Oct. 7, 2014

(54) PROCESS FOR THE PREPARATION OF LURASIDONE HYDROCHLORIDE

(71) Applicant: Edmond Pharma s.r.l., Paderno Dugnano (IT)

(72) Inventors: Matteo Zacche', Nerviano (IT); Fulvio Gerli, Paderno Dugnano (IT); Pierandrea Gatti, San Genesio Ed Uniti (IT)

(73) Assignee: Edmond Pharma S.R.L., Paderno Dugnano (IT)

( * ) Notice: Subject to any disclaimer, the term of this patent is extended or adjusted under 35 U.S.C. 154(b) by 0 days.

(21) Appl. No.: 14/185,184

(22) Filed: Feb. 20, 2014

(65) Prior Publication Data

US 2014/0243529 A1   Aug. 28, 2014

(30) Foreign Application Priority Data

Feb. 22, 2013   (IT) .......................... MI2013A000262

(51) Int. Cl.
*C07D 471/10* (2006.01)
*C07D 487/10* (2006.01)
*C07D 417/12* (2006.01)

(52) U.S. Cl.
CPC .................................. *C07D 417/12* (2013.01)
USPC ........................................... 544/231; 544/368

(58) Field of Classification Search
USPC ................................... 544/231, 368
See application file for complete search history.

(56) References Cited

U.S. PATENT DOCUMENTS 5,532,372 A * 7/1996 Saji et al. ...................... 544/368
8,586,737 B2 * 11/2013 Ae et al. ........................ 544/231

* cited by examiner

*Primary Examiner* — Bruck Kifle
(74) *Attorney, Agent, or Firm* — Silvia Salvadori, P.C.

(57) ABSTRACT

Disclosed is a new and efficient process for the synthesis with high yields and purity of lurasidone hydrochloride, a medicament which is useful as a psychotropic substance. The process involves the preparation of lurasidone base in a reaction system not containing inorganic salts, followed by conversion of the latter to an addition salt with an organic carboxylic acid, which is finally converted to lurasidone hydrochloride.

14 Claims, No Drawings

PROCESS FOR THE PREPARATION OF LURASIDONE HYDROCHLORIDE

This U.S. Non-Provisional Application claims priority to and the benefit of Italian Application No. MI2013A000262 filed on Feb. 22, 2013, the content of which is incorporated by reference in its entirety.

FIELD OF INVENTION

The present invention relates to a new process for the synthesis of lurasidone hydrochloride.

BACKGROUND TO THE INVENTION

Lurasidone hydrochloride, which has the chemical name ((3aR,4S,7R,7aS)-2-[((1R,2R)-2-{[4-(1,2-benzisothiazol-3-yl)-piperazin-1-yl]methyl}cyclohexyl)-methyl]hexahydro-1H-4,7-methanisoindol-1,3-dione hydrochloride, and is represented by formula 1

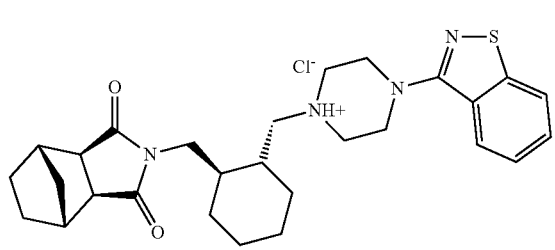

is an atypical antipsychotic used in the treatment of schizophrenia and bipolar disorders.

Lurasidone and a process for its preparation are disclosed in U.S. Pat. No. 5,532,372, wherein a compound of formula 2

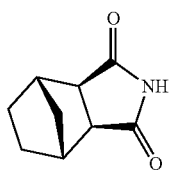

and a quaternary ammonium salt of formula 3

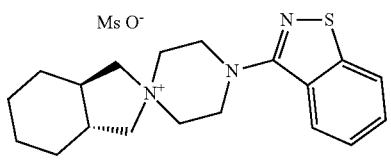

are reacted by refluxing a mixture thereof in xylene in the presence of dibenzo-18-crown-6-ether and potassium carbonate. The free base obtained is then reacted with gaseous hydrochloric acid to form the hydrochloride.

This process has many drawbacks; for example, dibenzo-18-crown-6 is a highly toxic, expensive substance and is not suitable for drug manufacturing nor for industrial production. Moreover, the use of alkali metal carbonates such as potassium carbonate results in the formation of a by-product or series of by-products containing the carbonate moiety. Additionally, the reaction system is heterogeneous, so it is difficult to maintain stable reaction times on an industrial scale. Finally, the use of gaseous hydrochloric acid is hard to apply on an industrial scale because it has many drawbacks in terms of safety of operators, equipment and the environment.

A similar method for preparing lurasidone is disclosed in patent application US 2011/0263847. Said patent describes the synthesis of the compound of formula 3 as a first step, by reacting a compound of formula 4 with a compound of formula 5 in toluene with a solid inorganic base such as potassium carbonate

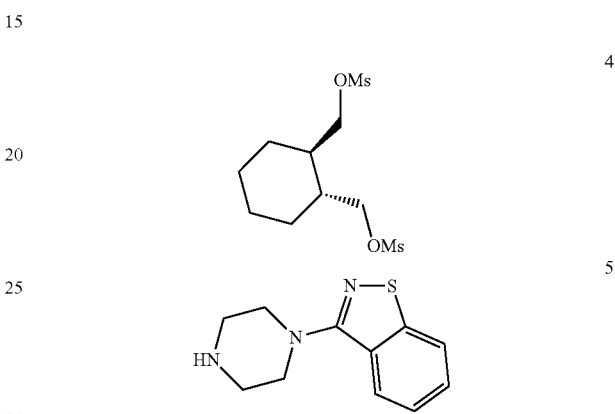

In the second step, a compound of formula 2 is then added to the quaternary ammonium salt 3 obtained in the same reaction vessel, and reacted with a solid organic base to obtain lurasidone.

This process also suffers from the same drawbacks as the previous one, i.e. the formation of a carbonate impurity, which is described in the patent application as a "by-product (R)", and the reaction medium is still heterogeneous. Moreover, the desired product is obtained in a mixture with inorganic salts, making it necessary to perform solvent extractions and subsequent purifications to isolate lurasidone. This process is clearly difficult to scale up to an industrial scale.

Another method is disclosed in US patent application 2011/0263848. This document describes the same process as US 2011/0263847, but using a phosphate salt during the preparation of compound 3 (first step), while the second step, i.e. the lurasidone formation reaction, is still performed with potassium carbonate. This process still suffers from the same drawbacks as US 2011/0263847, i.e. a heterogeneous reaction system and formation of "by-product (R)".

There is thus a need for an efficient process for the preparation of lurasidone hydrochloride which uses less toxic reagents, and can be applied on an industrial scale without the formation of impurities which are hard to remove.

DESCRIPTION OF THE INVENTION

The present invention provides an improved process for the preparation of lurasidone hydrochloride which has significant improvements on the process described in the prior art. It has surprisingly been found that lurasidone base can be prepared in a reaction system free from inorganic salts and thus obtained free from related by-products. Said crude lurasidone base can surprisingly be purified by conversion to an organic carboxylic acid addition salt to obtain very efficient purification in terms of purity and yield. The acid addition salt is then converted to lurasidone hydrochloride, which is suitable as an API for pharmaceutical production.

In the first step of the process according to the invention, lurasidone base can be prepared by reacting, in a high boiling point solvent, a compound of formula 4 with a compound of formula 5 in the presence of an organic base to prepare a compound of formula 3, and then, without isolating the compound of formula 3, by reacting it in the same reaction medium with a compound of formula 2, in the presence of an organic base. The compound of formula 3 may optionally be isolated from the reaction medium, but it is more practical from an industrial point of view to proceed with the one-pot reaction.

A molar ratio between the compound of formula 4 and the compound of formula 5 ranging between 0.5 and 1.5, preferably between 0.8 and 1.2, is used.

A molar ratio between the compound of formula 2 and the compound of formula 4 ranging between 0.5 and 1.5, preferably between 0.8 and 1.2, is used.

The organic base used for the reaction is selected from organic bases with a $pK_B$ higher than 10. Suitable bases include, for example, 1,4-diazabicycloundec-7-ene (DBU), 1,5-diazabicyclo[4.3.0]non-5-ene (DBN), 1,4-diazabicyclo[2.2.2]-octane (DABCO), diminazen, benzamidine, and non-nucleophilic organic bases in general (such as phosphazenes, amidines and guanidines). Particularly advantageous from an industrial point of view is the use of DBU, because it is readily available at low cost, and is therefore used in a preferred embodiment of the present invention.

A molar ratio between the organic base and compound 4 ranging between 0.8 and 3 is used in the first stage of the reaction, and a molar ratio between the organic base and compound 2 ranging between 0.8 and 3 is used in the second stage thereof.

Said reaction is carried out in an organic solvent with a boiling point higher than 80° C. Suitable solvents include, for example, toluene, xylene, 1,4-dioxane, dimethyl sulphoxide, or mixtures thereof. In a preferred embodiment, the solvent is 1,4-dioxane or a mixture of 1,4-dioxane and dimethyl sulphoxide.

The temperature of the reaction is kept between 80° C. and 190° C., preferably between 100° C. and 140° C. In this range, it is possible to maintain a stable homogeneous reaction system, with a total reaction time suitable for industrial production, while maintaining a low impurity profile. Higher temperatures would result in a higher impurity profile, while lower temperatures would result in lengthy reaction times.

At the end of the reaction, crude lurasidone base is isolated by methods known in the art, such as solvent extraction or anti-solvent precipitation. In a preferred embodiment, the product is isolated by anti-solvent precipitation. Said anti-solvent may be, for example, a ketone, an alcohol, water, or mixtures thereof.

In the second step of the process described in the present invention, lurasidone base is purified by conversion to an acid addition salt with an organic carboxylic acid having a $pK_A$ lower than 3. Such purification is highly efficient in removing almost all organic impurities from the product, and produces a lurasidone salt with very high purity and higher yields than the methods described in the prior art.

Carboxylic acids suitable for the purposes of the present invention include, for example, tartaric acid, pyruvic acid, maleic acid, oxalic acid and dihydroxy-fumaric acid.

A molar ratio between the organic carboxylic acid and lurasidone base ranging between 0.5 and 1.5, preferably between 0.8 and 1.2, is used.

In a preferred embodiment, oxalic acid is used, because it is more suitable for industrial production. Lurasidone oxalate is thus obtained by mixing the crude lurasidone base obtained in the first step with oxalic acid in an appropriate solvent. The oxalic acid used can be in the anhydrous, monohydrate or dihydrate form, the dihydrate being the preferred form.

The temperature is kept between 0° C. and the reflux temperature of the solvent. The mixture is preferably heated to reflux for an appropriate amount of time or until complete dissolution, and then cooled to a temperature ranging between 0° C. and 25° C., thus allowing the product to crystallise.

The solvent is selected from alcohols, ketones, alkyl acetates, halogenated hydrocarbons, ethers and water. The solvent is preferably selected from isopropanol and acetone, which provide the highest yields with the lowest impurity profiles.

The product is then isolated by filtration or other similar methods known in the art.

In the third step of the process described in the present invention, the acid addition salt obtained as above is converted to lurasidone hydrochloride, which is a suitable API for the production of a pharmaceutical composition. The reaction is carried out by mixing the acid addition salt of lurasidone, preferably lurasidone oxalate, in a suitable solvent and adding hydrochloric acid (gaseous or in solution) to the resulting solution or suspension.

The temperature is kept between 0° C. and the reflux temperature of the solvent. The mixture is preferably heated to reflux for an appropriate amount of time or until dissolution, and then cooled to a temperature ranging between 0° C. and 25° C., thus allowing the product to crystallise.

The solvent is selected from alcohols, ketones, alkyl acetates and water, or mixtures thereof. The solvent is preferably selected from methanol, ethanol, acetone and water, or mixtures thereof.

The hydrochloric acid used may be gaseous or in solution; preferably in solution, which has many industrial advantages, as already stated. More preferably, the hydrochloric acid is used in the form of an aqueous solution. Even more preferably, a concentrated solution is used, which is readily available on an industrial scale.

The product thus obtained is then isolated by filtration or other similar methods known in the art.

In a preferred embodiment, therefore, lurasidone hydrochloride is prepared by a process which comprises:

reacting a compound of formula 4 and a compound of formula 5 in a 1,4-dioxane/dimethylsulphoxide mixture using DBU as a base at a temperature ranging between 100° C. and 140° C., until a compound of formula 3 is formed;

adding a compound of formula 2 and DBU to the resulting solution and heating to 120-140° C. until lurasidone is obtained;

adding an anti-solvent, such as a mixture of a ketone and water or an alcohol and water, to the resulting solution to isolate crude lurasidone base;

purifying the lurasidone base thus obtained by mixing it with oxalic acid in isopropanol or acetone, heating the mixture to reflux until a solution is obtained, then cooling to about 20° C. and isolating pure lurasidone oxalate by filtration;

dissolving the pure lurasidone oxalate thus obtained by heating in a solvent selected from methanol, acetone, ethanol, water or mixtures thereof, then adding concentrated hydrochloric acid and cooling the solution, thus allowing lurasidone hydrochloride to crystallise, after which it is collected by filtration.

The lurasidone hydrochloride obtained by the process according to the invention is free from unknown impurities above 0.1%, and is therefore suitable for use as an API for the preparation of a pharmaceutical form ready for administration.

The present invention discloses a simple, economical, efficient, robust, environment-friendly process for the manufacture of lurasidone hydrochloride of formula 1 with high yields and high purity, which is suitable for use on an industrial scale.

The invention will now be further illustrated by the following examples.

Example 1

Synthesis of Lurasidone Base 177 g of compound 4 and 150 g of compound 5 are added to a mixture consisting of dioxane (250 mL) and dimethyl sulphoxide (250 mL). The mixture is heated to a reflux temperature of 120° C., and a total of 192 g of DBU is added in four portions every 20 minutes. After six hours, a further 20 g of DBU is added, and heating continues for a further three hours. 125 g of compound 2 and 228 g of DBU are added to the solution of compound 3 thus obtained, and the mixture is heated to 140° C., distilling about 50 mL of solvent. After eight hours' heating at said temperature the mixture is cooled to ambient temperature and diluted with 6 L of an acetone/water 1:2 mixture, and the lurasidone base thus obtained is isolated by filtration (190 g).

Example 2

Synthesis of Lurasidone Base 480 g of compound 4 and 400 g of compound 5 are added to a mixture consisting of dioxane (960 mL) and dimethyl sulphoxide (48 mL). The mixture is heated to the reflux temperature of 106° C., and 560 g of DBU is dripped into it in 60 minutes. After ten hours' heating, 280 g of compound 2 and 560 g of DBU are added to the solution of compound 3 thus obtained and heated to 125-130° C., distilling about 300 mL of solvent. After ten hours' heating at said temperature 40 mg of DBU is added, and heating continues for a further 12 h. The mixture is then cooled to ambient temperature, diluted with 14 L of an acetone/water 1:2 mixture, and the lurasidone base (450 g) is filtered and dried.

Example 3

Synthesis of Lurasidone Oxalate

A mixture consisting of isopropanol (600 mL), lurasidone base (57 g) and oxalic acid dihydrate (15 g) is refluxed for about an hour, and then cooled for two hours at ambient temperature. The solid is filtered, and 62 g of substantially pure lurasidone oxalate is obtained after drying.

Example 4

Synthesis of Lurasidone Oxalate

A mixture consisting of acetone (4750 mL) and lurasidone base (431 g) is refluxed until dissolved. Oxalic acid dihydrate (110 g) is added, and the mixture is cooled to ambient temperature, and then cooled for two hours at 10° C. The solid is filtered, and 435 g of substantially pure lurasidone oxalate is obtained after drying.

Example 5

Synthesis of Lurasidone Hydrochloride

A mixture consisting of acetone (3450 mL) and lurasidone oxalate (432 g) is refluxed until dissolved. Concentrated hydrochloric acid (68 mL) is added, and the mixture is cooled to ambient temperature, and then cooled for three hours at 5° C. The solid is filtered, and 326 g of lurasidone hydrochloride free of impurities exceeding 0.1% is obtained after drying.

Example 6

Synthesis of Lurasidone Hydrochloride

A mixture consisting of acetone (280 mL), water (140 mL) and lurasidone oxalate (47 g) is refluxed until dissolved. Concentrated hydrochloric acid (11 mL) is added, and the mixture is cooled at ambient temperature for two hours. The solid is filtered, and 36 g of lurasidone hydrochloride free of impurities exceeding 0.1% is obtained after drying.

The invention claimed is:
1. Process for the preparation of lurasidone hydrochloride of formula 1

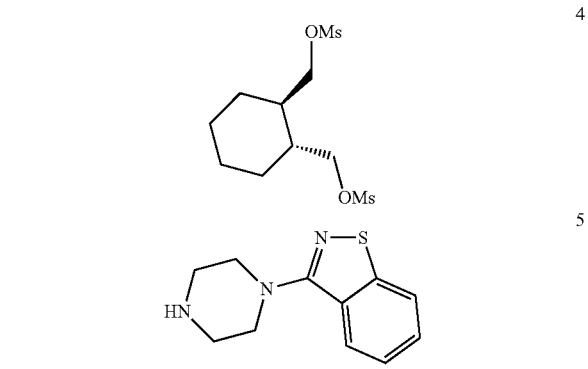

comprising the following steps:
a) reacting a compound of formula 4 and a compound of formula 5 in a solvent having a boiling point greater than 80° C. in the presence of an organic base having a $pK_B$ greater than 10, to yield a compound of formula 3

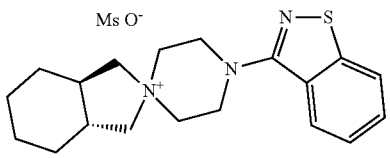

b) reacting the compound of formula 3 obtained in step a) with a compound of formula 2

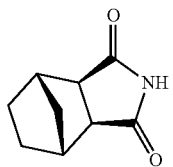

in a solvent having a boiling point greater than 80° C. in the presence of an organic base having a $pK_B$ greater than 10, to yield lurasidone base;

c) converting lurasidone base to an acid addition salt of lurasidone with an organic carboxylic acid having a $pK_A$ lower than 3;

d) converting the acid addition salt of lurasidone obtained in step c) to lurasidone hydrochloride.

2. The process of claim 1, wherein the compound of formula 2 is added directly to the reaction mixture obtained in step a), without isolating the compound of formula 3.

3. The process of claim 1, wherein the compound of formula 3 is isolated.

4. The process of claim 1, wherein step a) is performed at the temperature of 80-190° C.

5. The process of claim 1, wherein step b) is performed at the temperature of 80-190° C.

6. The process of claim 1, wherein the solvent having a boiling point higher than 80° C. is selected from the group of toluene, xylene, 1,4-dioxane and dimethyl sulphoxide, or mixtures thereof.

7. The process of claim 1, wherein the organic base having a $pK_B$ greater than is selected from the group of 1,4-diazabicycloundec-7-ene, 1,5-diazabicyclo[4.3.0]non-5-ene, 1,4-diazabicyclo[2.2.2]octane, diminazen and benzamidine.

8. The process according to claim 1, wherein step c) comprises the conversion of lurasidone base to a salt with an organic carboxylic acid selected from the group of tartaric acid, pyruvic acid, maleic acid, oxalic acid and dihydroxyfumaric acid.

9. The process according to claim 8, wherein lurasidone base is converted to lurasidone oxalate.

10. The process according to claim 1, wherein step c) comprises the conversion of lurasidone base to lurasidone oxalate, which is converted to lurasidone hydrochloride with hydrochloric acid, used either in gaseous form or in solution.

11. The process of claim 1, wherein step a) is performed at the temperature of 100-140° C.

12. The process of claim 1, wherein step b) is performed at the temperature of 120-140° C.

13. The process of claim 6 wherein the solvent is 1,4-dioxane or a mixture of 1,4-dioxane and dimethyl sulphoxide.

14. The process of claim 7, wherein the organic base is 1,4-diazabicyclundec-7-ene.

* * * * *